United States Patent [19]

Behre et al.

[11] 4,426,334
[45] Jan. 17, 1984

[54] PROCESS FOR ISOLATING H ACID AND K ACID

[75] Inventors: Horst Behre; Heinz U. Blank, both of Odenthal; Otto Lindner, Bergisch Gladbach; Willi Schössler, Cologne, all of Fed. Rep. of Germany

[73] Assignee: Bayer Aktiengesellschaft, Leverkusen, Fed. Rep. of Germany

[21] Appl. No.: 368,194

[22] Filed: Apr. 14, 1982

[30] Foreign Application Priority Data

May 7, 1981 [DE] Fed. Rep. of Germany ....... 3118147

[51] Int. Cl.³ ............................................ C07C 143/48
[52] U.S. Cl. .................................................... 260/509
[58] Field of Search ......................................... 260/509

[56] References Cited

U.S. PATENT DOCUMENTS

| 4,111,979 | 9/1978 | Kotera et al. | 260/509 |
| 4,166,826 | 9/1979 | Schössler et al. | 260/509 |
| 4,178,308 | 12/1979 | Schössler et al. | 260/509 |
| 4,325,889 | 4/1982 | Behre et al. | 260/509 |

Primary Examiner—Nicky Chan
Attorney, Agent, or Firm—Sprung, Horn, Kramer & Woods

[57] ABSTRACT

The invention relates to a process for isolating H acid and K acid in the form of their monoalkali metal salts from acid aqueous solutions which contain these two acids and alkali metal ions and may contain other aminonaphtholdisulphonic acids, in which process H acid monoalkali metal salts are precipitated at elevated temperatures from solutions which contain not only sodium ions but also potassium ions and then precipitating K acid monoalkali metal salts by cooling down the filtrate obtained after separating off the H acid monoalkali metal salts.

6 Claims, No Drawings

PROCESS FOR ISOLATING H ACID AND K ACID

The invention relates to an improved process for isolating H acid and K acid from mixtures containing these two acids.

H acid (1-amino-8-naphthol-3,6-disulphonic acid) and K acid (1-amino-8-naphthol-4,6-disulphonic acid) are important intermediate products in the preparation of dyestuffs (see Ullmanns Enzyklopädie der Technischen Chemie [Ullmann's Encyclopaedia of Industrial Chemistry], 4th edition, Volume 17, page 106).

In previous processes for their preparation, the two acids were obtained by alkaline pressure hydrolysis of the corresponding naphthylaminetrisulphonic acids, H acid being obtained from T acid (1-naphthylamine-3,6,8-trisulphonic acid) and K acid from melanic acid (1-naphthylamine-4,6,8-trisulphonic acid).

German Offenlegungsschrift No. 2,843,680 describes a process for the preparation of monoalkali metal salts of K acid, in which process a mixture of isomeric naphthylaminetrisulphonic acids containing melanic acid and T acid as main constituents and/or their salts are reacted under an elevated pressure and at an elevated temperature with alkali metal hydroxide solutions and, after the alkaline reaction solutions have been acidified, H acid and K acid are separated off as monoalkali metal salts either separately and successively by fractional crystallisation at various temperatures, or as a mixture at one temperature and the mixture is then split into K acid and H acid by a fractional dissolving out of K acid.

However, the method used in this process for isolating H acid and K acid from mixtures which contain these two acids as well as other isomeric aminonaphtholsulphonic acids and a number of other compounds is still not satisfactory in respect of the yield and purity of the H acid and the K acid thus obtained.

It has now been found that it is possible to improve considerably not only the yields but also the purity of H acid and K acid when isolating them from mixtures which contain the two acids and which may also contain other isomeric aminonaphtholsulphonic acids, not by precipitating H acid and K acid, as used to be the case, from acid solutions which contain only the ions of one alkali metal, namely either only sodium ions or only potassium ions, but by precipitating H acid from acid solutions which contain not only sodium ions but also potassium ions.

The invention therefore relates to a process for isolating H acid and K acid in the form of their monoalkali metal salts from acid aqueous solutions which contain these two acids and alkali metal ions and which may contain other aminonaphtholdisulphonic acids, by precipitating H acid monoalkali metal salts at elevated temperatures and precipitating K acid monoalkali metal salts by cooling down the filtrate obtained on separating off the H acid, which process is characterised in that the H acid is precipitated from solutions which contain not only sodium ions but also potassium ions.

In the acid solutions, the ratio of sodium ions to potassium ions is advantageously of 5–1:1, preferably 3–2:1.

For the precipitation of H acid the total concentration of alkali metal ions in the acid solutions is advantageously 1–10 g atoms/l of solution, preferably 3–8 g atoms/l of solution.

By precipitating H acid from acid solutions which contain not only sodium ions but also potassium ions the H acid precipitates in the form of mixed monosodium-monopotassium salts. These mixed sodium-potassium salts of H acid surprisingly have a considerably lower solubility than the monosodium and monopotassium salts of H acid. Because the mixed monosodium-monopotassium salts of H acid are sparingly soluble, H acid is not only precipitated almost quantitatively and in a high purity from the solution which contains the H acid and K acid, but at the same time K acid is obtained in higher yields and in higher purity, since no H acid, which would impair the precipitation, is present any longer in the solution when the K acid is precipitated.

Compared with the process for isolating H acid and K acid described in German Offenlegungsschrift No. 2,843,680, a yield increase from 62 to 70% for H acid and a yield increase from 70 to 75% by weight for K acid are obtained. Furthermore, in the process according to the invention, H acid and K acid are obtained in a higher purity.

To precipitate the H acid in form of its mixed monosodium-monopotassium salts, the pH of the solutions which contain H-acid and K acid and which may also contain other aminonaphtholdisulphonic acids is adjusted by the addition of mineral acids to a value of 0 to 4, preferably 0.5 to 2.5.

H acid is preferably precipitated from acid aqueous solutions, the solids content (total of aminonaphtholdisulphonic acids and alkali metal salts) of which is about 10 to 60% by weight, preferably 20 to 50% by weight.

The solids content of the filtrates from which K acid is precipitated is advantageously 10 to 60% by weight, preferably 20 to 50% by weight.

H acid is precipitated from acid solutions in the form of its mixed monosodium-monopotassium salts at temperatures of 20° to 100° C., preferably 30° to 90° C. and, in particular, 40° to 60° C. The precipitated H acid is separated mechanically from the solution, for example by filtering or centrifuging. The separated-off product is washed with an aqueous alkali metal sulphate solution and/or with water and then dried, if appropriate in vacuo. The wash liquors are reused instead of water in a subsequent batch.

K acid is precipitated from the acid filtrates obtained after the H acid monoalkali metal salts have been separated off. This is carried out by cooling down the acid filtrate, after the content of sodium ions has been adjusted to a concentration of 1 to 10 g atoms/l of filtrate, preferably 2 to 6 g atoms/l of filtrate, if necessary by the addition of compounds which donate sodium ions, for example of sodium salts, such as sodium chloride, sodium sulphate or sodium hydrogen sulphate, to a temperature below the precipitation temperature of H acid. Depending on the temperature at which the H acid was precipitated, the K acid is precipitated at temperatures from −5° to 40° C., preferably 10° to 30° C. and, in particular, 15° to 25° C. After the precipitation is complete, the K acid monoalkali metal salt is mechanically separated from the solution, for example by filtering or centrifuging. The separated-off product is washed with aqueous sodium sulphate or sodium chloride solution and/or water and then dried, if appropriate in vacuo. The wash liquors are reused instead of water in a subsequent batch.

The ratios according to the invention of sodium ions to potassium ions in the acid solutions intended for precipitating H acid can be established in various ways. In the simplest case this is done by adding to the alkaline solutions obtained in the pressure hydrolysis of naphthylaminetrisulphonic acids with sodium hydroxide or potassium hydroxide, before, during or after the acidifying with mineral acids, the missing alkali metal ion type in the form of compounds which donate these alkali metal ions, for example potassium ions, preferably in the form of potassium salts, such as potassium chloride or potassium sulphate or potassium hydrogen sulphate, or sodium ions, preferably in the form of sodium salts, such as sodium chloride, sodium sulphate or sodium hydrogen sulphate. However, the ion ratio according to the invention can also already be established in an earlier process phase by hydrolysing the naphthylaminetrisulphonic acids and/or their sodium salts or potassium salts with a mixture of sodium hydroxide solution and potassium hydroxide solution which corresponds to the sodium ion/potassium ion ratio desired or with the corresponding amounts of sodium hydroxide solution or potassium hydroxide solution respectively, so that the sodium/potassium ion ratio according to the invention is already present in the hydrolysis mixture.

The process according to the invention for separating off H acid and K acid from solutions which contain these two acids and which may also contain other aminonaphtholdisulphonic acids can be used for isolating H acid and K acid from solutions which contain H acid and K acid in widely varying weight ratios. In the solutions, the weight ratio of H acid to K acid can vary between 1:6 and 6:1.

Of particular interest is the isolation of H acid and K acid from solutions which contain, relative to the aminonaphtholsulphonic acids contained therein, about 10 to 70% by weight of K acid, 70 to 10% by weight of H acid and about 1 to 25% by weight of other aminonaphtholdisulphonic acids as well as other quantitatively indeterminable compounds from the preceding steps in the preparation of mixtures of aminonaphtholdisulphonic acid isomers. Such solutions are obtained in the preparation of K acid by alkaline pressure hydrolysis of mixtures of crude melanic acid isomers, as described in German Offenlegungsschrift No. 2,843,680, or can be prepared by any other way desired.

EXAMPLE 1

761 g of a naphthylaminetrisulphonic acid mixture in the form of the trisodium salts (content of 9.07 g of total nitrite/100 g, 25.2% by weight of melanic acid of molecular weight 383; a total of 69 g of nitrite, 0.50 mol of melanic acid) of the following composition:
1-naphthylamine-4,6,8-trisulphonic acid: 50.0%
1-naphthylamine-3,6,8-trisulphonic acid: 29.6%
2-naphthylamine-4,6,8-trisulphonic acid: 8.8%,
1-naphthylamine-2,5,7-trisulphonic acid: 1.2%,
1-naphthylamine-3,5,7-trisulphonic acid: 2.5% and
2-naphthylamine-3,6,8-trisulphonic acid: 0.2%
(% content are in each case relative to diazotisable substance), which additionally contains 12.1% by weight of water and quantitatively indeterminable amounts of amino and nitro derivatives of dinaphthylsulphonesulphonic acids and of oxidation products of naphthalene and of naphthalenetrisulphonic acids, as well as 160 g (4.0 mols) of sodium hydroxide, 140 g (2.5 mols) of potassium hydroxide and 608 g of water are initially introduced into a 2.7 l nickel autoclave, whereby a 30% strength, relative to the total amount of water, alkali metal hydroxide solution is produced. The reaction mixture is heated to 170° C., maintained for 12 hours at 170° C., cooled down to 100° C., diluted with 1,930 g of water and acidified at 80° C. with maintenance of a pH value of 1 to 1.5 with about 800 g of 50% by weight strength sulphuric acid. To remove completely the sulphur dioxide still contained in the hydrolysis mixture, the mixture is heated for 30 minutes at 80° C. while nitrogen is being passed in. The mixture is then cooled down to 50° C. by evaporative cooling and further stirred for 2 hours at 50° C.

The precipitated product, the mixed monosodium-monopotassium salt of H acid, is filtered off at 50° C. and washed with a total of 200 g of a 15% strength by weight aqueous sodium sulphate solution.

Yield: about 180 g of moist product.

The composition of the moist product is determined by high pressure liquid chromatography; the product has the following composition (the percentages by weight indicated are relative to the free acids):
37.3% by weight of H acid,
0.6% by weight of K acid,
% by weight of iso-K acid (1-amino-6-naphthol-4,8-disulphonic acid),
% by weight of W acid (1-amino-6-naphthol-3,8-disulphonic acid),
% by weight of T acid (1-naphthylamine-3,6,8-trisulphonic acid),
0.2% by weight of chromotropic acid (1,8-dihydroxynaphthalene-3,6-disulphonic acid),
% by weight of dihydroxy-K acid (1,8-dihydroxynaphthalene-4,6-disulphonic acid) and remainder to 100% by weight: water, sulphate ions, sodium ions and potassium ions.

The yield of H acid is 21% of theory, relative to the nitrite content, or 71% of theory, relative to the T acid content of the naphthylaminetrisulphonic acid mixture used in the pressure hydrolysis.

To purify the moist crude product 180 g of it are suspended in 180 g of water, and the suspension is heated for 1 hour at 80° C., cooled down to 40° C. and further stirred for 2 hours at 40° C. The precipitated product is filtered off at 40° C., washed with a total of 75 g of water and dried at 60° C. in vacuo.

The yield is 81 g of dry product (when re-using the filtrate and the wash water in a subsequent batch); this corresponds to 70% of theory, relative to the T acid content of the naphthylaminetrisulphonic acid mixture used in the pressure hydrolysis.

The purity of the H acid is determined by high pressure liquid chromatography; the composition of the dry product is (the percentages by weight indicated are relative to the free acids):
81.9% by weight of H acid,
0.3% by weight of K acid,
% by weight of iso-K acid,
% by weight of W acid,
% by weight of T acid,
0.2% by weight of chromotropic acid and
% by weight of dihydroxy-K acid.
The product also contains
10.0% by weight of water,
4.5% by weight of potassium,
3.0% by weight of sodium and
0.2% by weight of sulphate.

428 g of sodium sulphate are added at 50° C. to the filtrate (4,280 g) obtained on filtering off the crude mixed monosodium-monopotassium salt of H acid, and the mixture is cooled down to room temperature (20° C.) and maintained at room temperature (20° C.) for 12 hours.

The precipitated K acid monosodium salt is filtered off, washed with a total of 300 g of a 15% by weight strength aqueous sodium sulphate solution and dried at 60° C. in vacuo.

The yield is 194 g of dry product, which corresponds to 35.5% of theory, relative to the nitrite content, or 71% of theory, relative to the melanic acid content of the naphthylaminetrisulphonic acid mixture employed.

The purity of the K acid is determined by high pressure liquid chromatography; the K acid has the following composition (the percentages by weight indicated are relative to the free acids):
58.3% by weight of K acid,
% by weight of H acid,
1.2% by weight of iso-K acid,
% by weight of W acid,
% by weight of melanic acid,
% by weight of T acid,
1.0% by weight of dihydroxy-K acid
% by weight of chromotropic acid and remainder to 100% by weight: water, sodium ions and sulphate ions.

EXAMPLE 2

The procedure described in Example 1 is followed, except for the modification that, to precipitate the K acid, 10 g of sodium chloride per 100 g of filtrate are added at 60° C. to the filtrate obtained on filtering off the crude H acid. The precipitated K acid monosodium salt is washed after it has been filtered off with a total of 300 g of a saturated sodium chloride solution.

The yield of crude K acid is 37.5% of theory, relative to the nitrite content, or 75% of theory, relative to the melanic acid content of the naphthylaminetrisulphonic acid mixture used in the pressure hydrolysis.

The purity of the K acid is determined by high pressure liquid chromatography; the composition of the K acid is (the percentages by weight indicated are relative to the free acids):
62.7% by weight of K acid,
% by weight of H acid,
3.5% by weight of iso-K acid,
0.6% by weight of dihydroxy-K acid and
remainder to 100% by weight: water, sodium ions and chloride ions.

To purify the crude product 150 g of it are suspended in 150 g of water, and the suspension is heated at 80° C., cooled down to 20° C. and further stirred for 2 hours at 20° C. The product is filtered off, washed with a total of 75 g of cold water and dried at 60° C. in vacuo.

The yield is 112 g of dry product (when returning the filtrate obtained on filtering off the K acid and the wash water obtained on washing); this corresponds to 73% of theory, relative to the melanic acid content of the naphthylaminetrisulphonic acid mixture employed.

The purity of the purified K acid is determined by high pressure liquid chromatography; the composition of the K acid is (the percentages by weight indicated are relative to the free acids):
81.4% by weight of K acid,
% by weight of H acid,
0.05% by weight of iso-K acid and
0.1% by weight of dihydroxy-K acid.

The product also contains
14.0% by weight of water,
3.7% by weight of sodium,
0.9% by weight of chloride and
110 ppm of potassium.

EXAMPLE 3

740 g of a naphthylaminetrisulphonic acid mixture in the form of the trisodium salts (content of 9.33 g of total nitrite/100 g, 26.6% by weight of melanic acid of molecular weight 383; a total of 69 g of nitrite, 0.51 mol of melanic acid) of the following composition:
1-naphthylamine-4,6,8-trisulphonic acid: 51.4%
1-naphthylamine-3,6,8-trisulphonic acid: 30.9%,
2-naphthylamine-4,6,8-trisulphonic acid: 9.0%,
1-naphthylamine-2,5,7-trisulphonic acid: 1.2%,
1-naphthylamine-3,5,7-trisulphonic acid: 2.5% and
2-naphthylamine-3,6,8-trisulphonic acid: 0.2%
(% contents are in each case relative to a diazotisable substance), which additionally contains 8.1% by weight of water and quantitatively indeterminable amounts of other by-products as well as 260 g (6.5 mols) of sodium hydroxide and 547 g of water are reacted as described in Example 1.

After dilution of the hydrolysis mixture with 1,453 g of water, the alkaline reaction solution is allowed to run at 80° C. with stirring into a reaction flask simultaneously with about 900 g of 50% by weight strength sulphuric acid while a pH value of 1 to 1.5 is being maintained, into which flask a mixture of 261 g (1.5 mols) of potassium sulphate and 500 ml of water have been initially introduced.

The resulting acid solution is worked up as described in Example 1. H acid and K acid are obtained in the same yields and grades as in Example 1.

EXAMPLE 4

673 g of a naphthylaminetrisulphonic acid [trisodium salt] mixture (a total of 69 g of nitrite and 0.72 mol of melanic acid) of the following composition:

| | |
|---|---|
| 72.3% of melanic acid, | |
| 16.8% of T acid, | |
| 1.6% of 1-naphthylamine-3,5,7-trisulphonic acid and | relative to diazotisable substance |
| 6.5% of 2-naphthylamine-4,6,8-trisulphonic acid | | are reacted with 120 g (3.0 mols) of sodium hydroxide, 196 g (3.5 mols) of potassium hydroxide and 682 g of water, as described in Example 1, and the reaction mixture is worked up as follows:

Isolation of H acid 1,671 g of the alkaline reaction mixture (suspension) containing sodium sulphite are diluted with
1,529 g of water.
3,200 g of this clear dilute alkaline reaction solution are then added simultaneously with
1,020 g of 50% by weight strength sulphuric acid at 80° C. in the course of 1 hour while maintaining a pH value of 1 to 1.5 into a seven-necked flask containing
800 g of water.

The sulphur dioxide formed is driven off by passing in nitrogen for 30 minutes at 80° C. The reaction mixture (suspension) is then cooled down to 50° C. and further stirred for 2 hours at 50° C. The precipitated H acid is then filtered off and washed 2 times with 75 g of a saturated sodium sulphate solution in each case. 95 g of moist crude H acid are thus obtained.

Isolation of K acid

The filtrate obtained on filtering off the crude H acid and the wash solution obtained on washing out the crude H acid are combined and about 500 g of sodium chloride (10 g of sodium chloride/100 g of filtrate) are added at 50° C. with stirring. The mixture is cooled down to 20° C. and further stirred for about 12 hours at 20° C. The precipitated K acid is then filtered off, washed twice with 250 g of a saturated sodium chloride solution in each case and dried at 80° C. in vacuo.

About 326 g of crude dry K acid are obtained.

The yield of technically pure, dry K acid is 54.3% of theory, relative to the nitrite content, or 75% of theory, relative to the melanic acid content of the naphthylaminetrisulphonic acid mixture employed in the pressure hydrolysis.

The degree of purity of the K acid is likewise determined by high pressure liquid chromatography; the K acid has the following composition:
53.1% by weight of K acid,
1.0% by weight of H acid,
3.7% by weight of iso-K acid,
0.3% by weight of dihydroxy-K acid,
0.1% by weight of chromotropic acid,
% by weight of melanic acid,
% by weight of T acid and also
27% by weight of sodium chloride and
6% by weight of water.

Purification of the crude H acid 95 g of crude moist H acid are slurried in about 150 g of water. The mixture, which has a pH value of 1 to 1.5, is heated to 80° C. and maintained at this temperature for 1 hour, then cooled down to 40° C. and further stirred for 2 hours at this temperature. H acid is then filtered off and washed successively with 25 g of warm water at 40° C., 25 g of warm water at 20° C. and 25 g of ice water. The acid is then dried at 80° C. in vacuo. 45.8 g of pure dry H acid are obtained, which corresponds to a yield of 11.3% of theory relative to the total nitrite content, or 67% of theory, relative to the T acid content of the naphthylaminetrisulphonic acid mixture employed.

The degree of purity of the H acid is determined by high pressure liquid chromatography; the composition of the H acid is:

78.4% by weight of H acid,
0.7% by weight of K acid,
% by weight of iso-K acid,
% by weight of W acid,
% by weight of T acid,
% by weight of chromotropic acid,
% by weight of dihydroxy-K acid and also
0.6% by weight of sulphate,
11.7% by weight of water,
3.0% by weight of sodium and
4.8% by weight of potassium.

What is claimed is:

1. In the process for isolating H acid and K acid in the form of their monoalkali metal salts from acid aqueous solutions which contain these two acids and alkali metal ions and which may contain other aminonaphtholdisulphonic acids, by precipitating H acid monoalkali metal salts at elevated temperatures and precipitating K acid monoalkali metal salts by cooling down the filtrate obtained on separating off the H acid, the improvement comprising precipitating the H acid from a solution which contains not only sodium ions but also potassium ions the ratio of sodium ions to potassium ions being 5–1:1.

2. The process according to claim 1, wherein in the solution the ratio of sodium ions to potassium ions is 3–2:1.

3. The process according to claim 1, wherein for the precipitation of H acid the total concentration of alkali metal ions in the acid solution is 1 to 10 g atoms/1 of solution.

4. The process according to claim 1, wherein for the precipitation of K acid the concentration of sodium ions in the filtrate obtained on filtering off H acid is 1 to 10 g atoms/1 of filtrate.

5. The process according to claim 1, wherein for the precipitation of H acid the pH value of the acid solution is 0 to 4.

6. The process according to claim 1, wherein the solids content of the acid solution from which H acid and K acid are precipitated is 10 to 60% by weight.

* * * * *

UNITED STATES PATENT AND TRADEMARK OFFICE
CERTIFICATE OF CORRECTION

PATENT NO. : 4,426,334

DATED : January 17, 1984

INVENTOR(S) : Horst Behre, et al

It is certified that error appears in the above-identified patent and that said Letters Patent is hereby corrected as shown below:

```
Col. 3, line 40                    Delete "by" and insert --in--
Col. 4, lines 18, 22, 26,          Before "%" insert -- 0 --
51, 52, 53, 55, 20

Col. 5, lines 12, 14, 15,          Before "%" insert -- 0 --
16, 18, 40, 60

Col. 7, lines 21, 22               Before "%" insert -- 0 --

Col. 8, lines 3,4,5,6,             Before "%" insert  -- 0 --
7
```

Signed and Sealed this

Third Day of July 1984

[SEAL]

Attest:

GERALD J. MOSSINGHOFF

*Attesting Officer*   *Commissioner of Patents and Trademarks*